United States Patent
Pedro et al.

(10) Patent No.: US 7,872,761 B2
(45) Date of Patent: Jan. 18, 2011

(54) METHOD FOR RELIABLE OPTICAL COHERENCE TOMOGRAPHY SCANS OF VOLUMES OF RETINAL TISSUE

(75) Inventors: Justin Pedro, Waterloo (CA); Clive Hayward, Kingston (CA); Duncan McLean, Kingston (CA)

(73) Assignee: OTI Ophthalmic Techlogies Inc. (CA)

( * ) Notice: Subject to any disclaimer, the term of this patent is extended or adjusted under 35 U.S.C. 154(b) by 292 days.

(21) Appl. No.: 12/209,453

(22) Filed: Sep. 12, 2008

(65) Prior Publication Data

US 2009/0079994 A1 Mar. 26, 2009

Related U.S. Application Data

(60) Provisional application No. 60/972,369, filed on Sep. 14, 2007.

(51) Int. Cl.
*G01B 9/02* (2006.01)
(52) U.S. Cl. ....................................... 356/479
(58) Field of Classification Search ................. 356/479, 356/497; 250/227.19, 227.27; 351/209, 351/210
See application file for complete search history.

(56) References Cited

U.S. PATENT DOCUMENTS

| | | | | |
|---|---|---|---|---|
| 5,321,501 A * | 6/1994 | Swanson et al. | ............ | 356/479 |
| 6,377,349 B1 * | 4/2002 | Fercher | ...................... | 356/497 |
| 6,769,769 B2 * | 8/2004 | Podoleanu et al. | .......... | 351/221 |
| 7,330,273 B2 * | 2/2008 | Podoleanu et al. | .......... | 356/497 |
| 7,649,629 B2 * | 1/2010 | Rogers et al. | ................ | 356/479 |
| 2009/0005691 A1 * | 1/2009 | Huang et al. | ................. | 600/476 |

OTHER PUBLICATIONS

Cucu, Radu G. et al. "Combined confocal/en face T-scan-based ultrahigh-resolution optical coherence tomography in vivo retinal imaging". Optics Letters, vol. 31, No. 11, Jun. 1, 2006, pp. 1684-1686.*

* cited by examiner

*Primary Examiner*—Michael A Lyons
(74) *Attorney, Agent, or Firm*—Richard J. Mitchell; Marks & Clerk

(57) ABSTRACT

A method of building up a three dimensional OCT image of an object having a limited region sensitive to movement of a scanning beam performs an OCT scan in a scanning pattern that results in said limited region, typically the fovea of the eye, being scanned last.

16 Claims, 2 Drawing Sheets

METHOD FOR RELIABLE OPTICAL COHERENCE TOMOGRAPHY SCANS OF VOLUMES OF RETINAL TISSUE

FIELD OF THE INVENTION

This invention relates to the field of optical coherence tomography (OCT), and in particular to a method of obtaining repeatable OCT scans of an object, such as an eye, subject to sudden movement.

BACKGROUND OF THE INVENTION

Optical coherence tomography is a technique by which a partially transparent object, such as an eye, may be scanned in three dimensions using interferometric techniques to build up a complete three dimensional volume image of the eye. In time domain OCT, a sample beam from an interferometer defines a coherence gate in the region where the optical path difference is less than the coherence length. The sample beam is scanned over the eye, typically in a raster fashion, to obtain reflectance data at points in an X-Y plane located at a depth corresponding to the coherence gate. By moving the coherence gate in the Z direction, data from different X-Y planes can be obtained. In spectral OCT, a complete line of data in the Z direction can be obtained at each point in the X-Y plane. A typical time domain OCT apparatus is described in U.S. Pat. No. 6,769,769, the contents of which are herein incorporate by reference. U.S. Pat. No. 6,377,349, the contents of which are herein incorporated by reference, describes a method employing spectral OCT.

A number of scanning schemes are known as described in U.S. Pat. No. 5,321,501, the contents of which are also herein incorporated by reference. The eye can be scanned transversely (en face) in a raster fashion, with the coherence gate moved in the Z direction after each complete en face scan, or alternatively it can be scanned in the X-Z or Y-Z plane, to obtain a series of slices (B-scans) that are then assembled to produce a complete three dimensional image.

In order to build up a complete three dimensional volume image of the eye, it is important that the eye remain stationary. Absolute stability of the patient's eye is required. Normally the stoccatic movements of a patient's eye are not of great importance because the patient can be quickly trained to fixate on a target while the scan is performed. However when visible laser light is used to perform the scan, a patient's natural reaction is to follow the motion of the laser after it passes through their fovea (center of focus). One option would be to freeze the patient's eye, but that option is neither desirable nor feasible for a simple OCT scan.

SUMMARY OF THE INVENTION

The present invention employs a novel scanning pattern that minimizes the chances of the patient following the laser with their eye. This enables the production of reliable, repeatable and accurate optical coherence tomography (OCT) scans of the retina when using visible light. Typically, the object is the eye, in which case the limited region is the fovea, although it will be understood that the invention is applicable to other like situations.

According to the present invention there is provided a method of building up a three dimensional OCT image of an object having a limited region sensitive to movement of a scanning beam, comprising performing an OCT scan of the object, and wherein said OCT scan is performed in a scanning pattern that results in said limited region being scanned last.

In one embodiment, the laser traces a path obtaining frames from alternating exterior positions, moving in one or more frames at a time towards the center such that the last frames gathered are in the fovea. The laser can alternate scanning top and bottom, left and right, or some other intermediary angles as long as the intent of the pattern the laser scans is to scan the fovea last. In another embodiment, a spiral pattern is employed.

BRIEF DESCRIPTION OF THE DRAWINGS

The invention will now be described in more detail, by way of example only, with reference to the accompanying drawings, in which:—

DETAILED DESCRIPTION OF THE PREFERRED EMBODIMENTS

Figure 1:
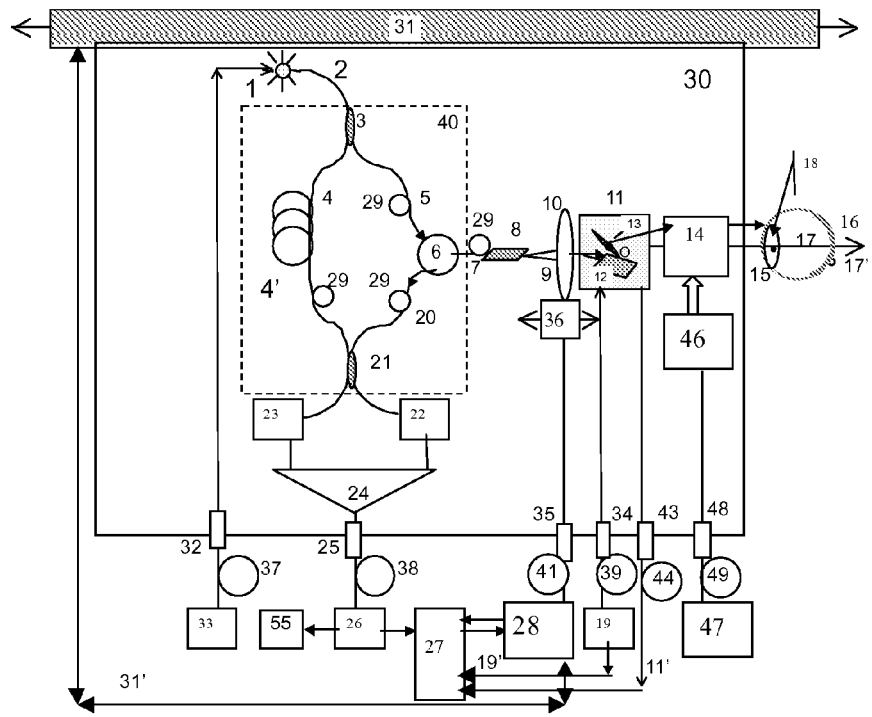
FIG. 1 is a block diagram of an exemplary OCT apparatus.

FIG. 1 diagrammatically shows the embodiment of a time domain OCT apparatus suitable for implementing the invention. The apparatus comprises an optical source, 1, which can be either low coherence or with adjustable coherence length, pigtailed to a single mode fiber, 2, wherefrom the power is split in a first optical splitter, which in FIG. 1 is shown as a directional single mode coupler, 3, into a reference beam, along the reference path 4 and an object beam, along the object path, 5. Light into the object path 5 is launched from the $1^{st}$ output of the first splitter and light into the reference path 4 is launched from the second output of the first splitter.

In the context of the invention, a low coherence source is a broadband source, whose coherence length is much less than the penetration depth of the radiation used in the object studied. Examples of such sources include superluminescent diodes, tungsten lamps, Kerr-lens mode-locked lasers, laser diodes below threshold and diverse combinations of the above. For instance, at the level of the technology today, the coherence length of such sources cover the range of 0.5-500 μm. In contrast, in the context of the invention, a high coherence source has a coherence length much larger than the penetration depth of the radiation used in the object studied. Examples of such sources include lasers, with a coherence length larger than 1 cm.

In the object path, a second optical splitter, 6, which in FIG. 1 is shown as an in-fiber circulator, is used to transfer light from the $1^{st}$ output of the first optical splitter and send light, via path 7 to output 8, terminated with a fiber connector at an angle, or cleaved at an angle, to minimize the fiber end reflection and in this way the noise. From the output 8, the light is sent via free space, 9, towards the focusing element 10, such as a refractive or reflective optical element and then deflected by a 2D scanner head 11, equipped with mirrors 12 and 13 to scan transversally, via interface optics 14, an object.

In FIG. 1 the object is the retina, 16, of an eye 17, in which case the beam is focused by the cornea 15 and eye lens 18 onto the retina 16. The line connecting the transverse scanning means and the object constitutes an optic axis of the apparatus, oriented along the deflected object beam in the middle of the scanning range of the transverse scanning means.

Scanner head 11 is a scanning assembly means known in the art and includes, for example, galvanometer scanners, piezo-vibrators, polygon mirrors, resonant scanners, acousto-optic modulators, rotating or vibrating prisms etc. Combinations of scanners from the list above can be used for the scanning pair head 11. One scanner usually works fast and the signal collected during its movement is displayed on the line in the raster of the final image, termed as the line scanner, while the other scanner, is typically termed as frame scanner. For instance, a polygon mirror can be used as the line scanner and a galvanometer scanner can be used as the frame scanner. The scanner head 11 is under the control of triangle, saw-tooth or DC voltages produced by a programmable computer controller 19, which determines the manner in which the scan is performed.

The scanning head 11 can be divided in two parts, namely the line scanner and the frame scanner, separated by optical elements like lenses and/or mirrors in configurations known in the art of scanning laser opthalmoscopes (SLO) and of confocal microscopy or general raster scanning systems, in which case the scanner head 11 and interface optics 14 are interleaved to each other, in one block, and only for convenience are they represented here separately. The scanner mirrors, 12 and 13, which refer to either galvanometer scanners or polygon mirrors have high reflectivity at the wavelength used, or if acousto-optic modulators are used, their transmission at the wavelength used is high. By means known in the art, the two scanners have orthogonal axes or scan the ray in perpendicular planes, producing a raster in the plane (X,Y), oriented perpendicular on the optic axis of the system. Circular scan, (ρ,θ) of the ray can also be obtained by sinusoidally scanning the ray using the two scanners in orthogonal directions at the same frequency with a phase difference of π/2, where ρ is determined by the amplitude of the angular deviation, measured in a plane perpendicular on the optic axis from the point hit by the ray when the scanners are not driven, and θ is a polar angle in this same plane.

Light returned from the object, via the interface optics 14, and then via the scanning head 11, is launched via the focusing elements 10 back into the second optical splitter 6, i.e. into the same port fiber, 7 of the circulator, 6, where the light originated from. The circulator routes the signal to the fiber output 20, which takes the signal to a first input of a third optical splitter 21, which in FIG. 1 is shown as a single mode directional coupler. The second input of the optical splitter 21 receives light from the reference path, 4, via a fiber delay line 4'.

The object signal interferes with the reference signal when the optical path difference (OPD) between the reference path length and the object path length is less than the coherence length of the source 1. This explains the selection in depth of the OCT. The reference path starts at the optical splitter 3 and ends at the optical splitter 21, and is made of fiber 4 and delay line 4'. The object path starts from the optical splitter 3 and again ends on the optical splitter 21, made out of fiber 5, circulator 6, fiber 7, fiber connector 8, free space path 9, focusing element 10, scanner head 11, interface optics 14 up to the object and back to the fiber 7. Points along the object beam in the volume of the object will contribute to the signal only from within the coherence length of the source in the volume of the object.

The embodiment in FIG. 1 has the advantage that the reference beam is all in fiber and no losses are incurred due to passing the light from fiber to free air and back, to allow for the adjustment of the reference path length. The OPD is adjusted instead on the expense of the object path length only. Such a configuration requires less assembly time, essential in series production. As fiber length compensates for the path in air in FIG. 1, dispersion may exist which may enlarge the depth sampling profile of the apparatus. However, it is known that single mode fiber at 1300 exhibits little dispersion.

To maximize the interference signal, polarization of light in the two arms of the interferometer needs to be the same. Therefore, at least a polarization controller 29 in one of the object path or reference path is required.

The optical splitter 21 is terminated on two photodetectors 22, 23 of a balanced photoreceiver unit 24. Preferably the splitter 21 needs to be an even 50/50 splitter for the whole band of wavelengths used, in order to achieve suitable reduction of the intensity noise and excess photon noise characteristic for low coherence sources. The photodetected signal obtained at the electrical connector output, 25, of the unit 24 is sent to the processing block 26 to provide strength proportional to the reflectivity, or the log version of the reflectivity, and then displayed and recorded by means of a suitable display device 27, such as a frame grabber, a storage oscilloscope or a suitable printer. The device 27 is under the control of computer 28. The block 26 contains a band pass filter followed by a rectifier and a low pass filter.

The filter is adjusted on two different functions depending on the regime of operation of the apparatus, as described below.

The apparatus can be typically operated in a number of regimes. In the T-scan regime, the transverse scanning means are used to move the object beam angularly or laterally in a time $T_H$ along a prescribed contour, which could be a horizontal line, a vertical line, a circular path, an elliptic path or any other open or closed path, while the translation stage is at rest, and a one dimensional en-face profile of the reflectivity versus the transverse position is obtained. In the embodiments of the apparatus equipped with a confocal receiver, the apparatus according to the invention acquires simultaneously a one dimensional en-face profile of the reflectivity versus the transverse position in the OCT channel and a one dimensional en-face profile of the reflectivity versus the transverse position in the confocal channel.

In the B-scan regime, the said translation stage is moved in steps after each T-scan to cover the depth range in a number of steps which determines the number of lines in the image frame, or the said translation stage is moved continuously in a time $T_B > T_H$ where the number of lines in the image frame is $T_B/T_H$, generating in this way a two dimensional map of reflectivity as a cross section through the object in a surface containing the optic axis and the T-scan contour.

In the C-scan regime, the transverse scanning means are used to move the beam angularly or laterally to cover a two dimensional pattern describing different shapes of T-scans in a time $T_C$ while the translation stage is kept fixed to generate a 2D map of reflectivity for constant depth in the reference path of the interferometer.

In the 3D-scan regime, the translation stage is moved in small steps after each C-scan to cover a depth range or at a constant speed less than the ratio determined by dividing the depth resolution to $T_C$, covering the depth range in a time $T_{3D}$ and a number $T_{3D}/T_C$ of C-scans are stored and then used to generate a 3D image of the interior of the object.

Figure 2:
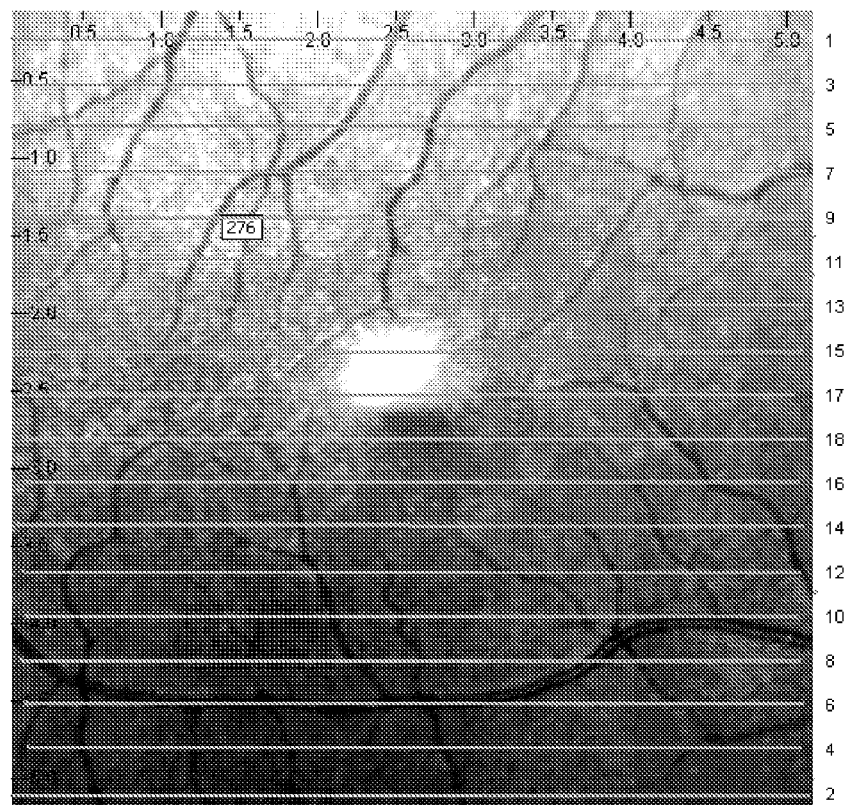
FIG. 2 shows a scanning strategy involving taking a series of B scans in a particular order.

In accordance with invention a scanning strategy is employed that results in the fovea being scanned last in order to minimize the effect of eye movement. The scanner head 11 is controlled to scan the eye in the pattern shown in FIG. 2. A series of B-scans (horizontal longitudinal slices) are obtained, but instead of scanning sequentially in a typical raster fashion, the scanning order is changed so that the sequence is as shown. The first scanning line is at the top of the image, the second at the bottom, the third is the next line down at the top, the fourth is the next line up at the bottom and so on, until the last scanning lines are obtained in the middle of the image which runs through the fovea. The resulting data is stored in memory to build up a three dimensional volume image of the object in a manner known per se.

Of course, other patterns can be employed that result in the fovea being scanned last. For example, it would be possible to start say at lines 11 and 18 and work alternately outwards, and on reaching the outer edge of the image return to scan the fovea by scanning lines 13, 17 and 15. It will be understood that the invention is also applicable to any other object that has a motion sensitive region.

The position of the scanning head 11 is computer controlled. The following algorithm will control the computer to move the scanning laser to create the pattern shown in FIG. 2.

```
Frame Separation = vertical scan angle / b scan frames required
Top Frame Position = 0;
Bottom Frame Position = maximum horizontal position
Move Laser to the top left
While (Top Frame Position < Bottom Frame Position)
{
    x = Left Most Position
    y = Top Frame Position
    Move laser to x,y
    Move laser to right most position gathering AScans to build a BScan
    Frame
    Store frame
    X = Right Most Position
    Y = Bottom Frame Position
    Move laser to x,y
    Move laser to right most position gathering AScans to build a bScan
    Frame
    Invert the frame left to right and store it.
    Top Frame Position = Top Frame Position + Frame Separation
    Bottom Frame Position = Bottom Frame Position − Frame Separation
}
```

An alternative is to create vertical B-scans, which can be achieved with the following algorithm:

```
Frame Separation = horizontal scan angle / b scan frames required
Left Frame Position = 0;
Right Frame Position = maximum vertical position
Move Laser to the top left
While (Left Frame Position < Right Frame Position)
{
    x = Left Frame Position
    y = Top Most Position
    Move laser to x,y
    Move laser to Bottom Most Position gathering AScans to build a BScan
    Frame
    Store frame
    X = Right Frame Position
    Y = Bottom Most Position
    Move laser to x,y
    Move laser to Top Most Position gathering AScans to build a bScan
    Frame
    Invert the frame left to right and store it.
    Left Frame Position = Left Frame Position + Frame Separation
    Right Frame Position = Right Frame Position − Frame Separation
}
```

Figure 3:
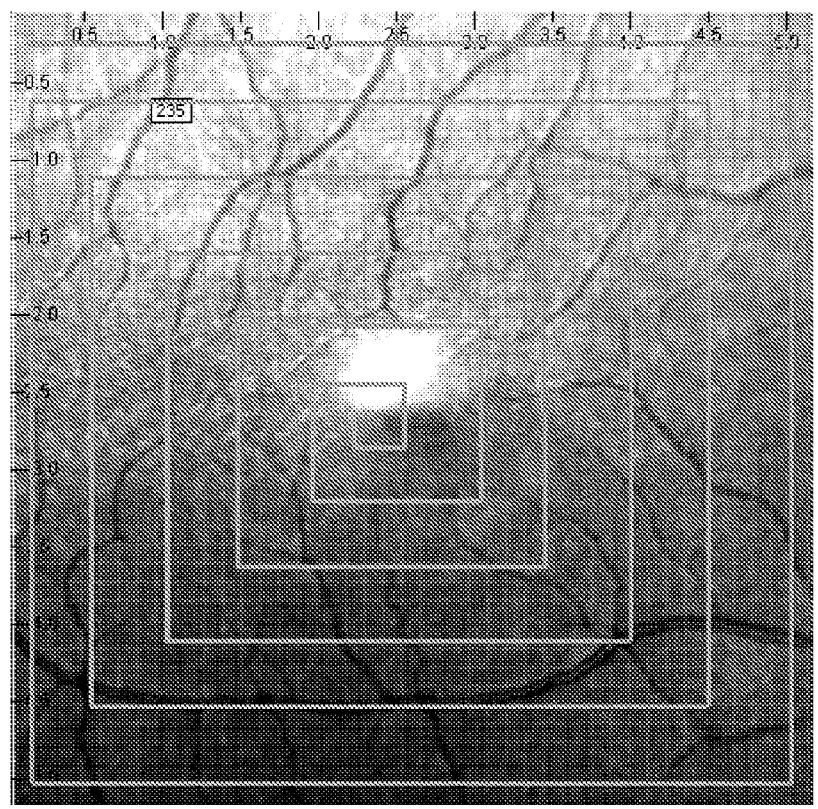
FIG. 3 shows a square spiral scanning pattern.
Figure 4:
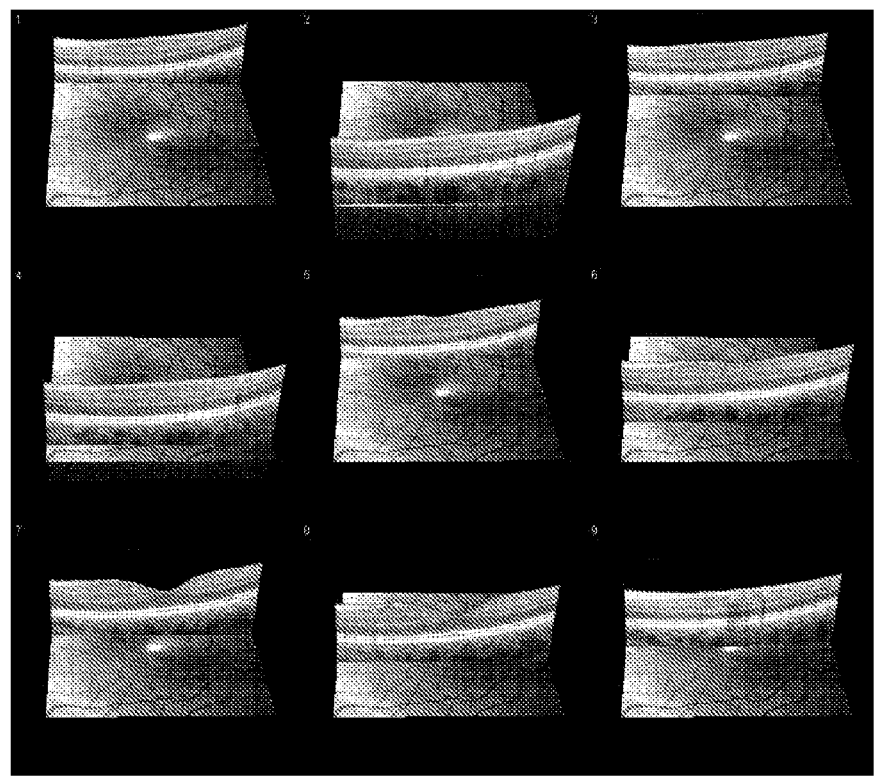
FIG. 4 shows a series of B-scans wherein the fovea is scanned last, and is a three dimensional representation of FIG. 2.

An alternative method is to employ a spiral pattern as shown in FIG. 3. In this case the scan pattern starts from the and terminates in the region of the fovea. The following algorithm will create this pattern:

```
Frame Separation = horizontal scan angle / b scan frames required
Left Frame Position = 0;
Right Frame Position = maximum vertical position
Top Frame Position = 0;
Bottom Frame Position = maximum horizontal position
Move Laser to the top left
While (Left Frame Position < Right Frame Position)
{
    x = Left Frame Position
    y = Top Frame Position
    Move laser to x,y
    x = Right Frame Position
    Move laser to x,y gathering AScans
    Y = Bottom Most Position
    Move laser to x,y gathering AScans
    X = Left Frame Position
    Move laser to x,y gathering AScans
    Top Frame Position = Top Frame Position + Frame Separation
    Y = Top Frame Position
    X = Left Frame Position
    Move laser to x,y gathering AScans
    Left Frame Position = Left Frame Position + Frame Separation
    Right Frame Position = Right Frame Position − Frame Separation
    Bottom Frame Position = Bottom Frame Position − Frame Separation
}
```

It will be appreciated that there are many different ways the laser beam can be moved around the retina such that the fovea is scanned last. The above techniques are merely examples. For example, the first two algorithms above could easily be varied to take 2, 3, or more frames in one area before moving to the next. For example, two frames from the top, two from the bottom, two more from near the top, two more from near the bottom, etc. They could also be easily modified to take frames on a diagonal. The latter algorithm could be varied to take consecutive square scans rather than the square spiral. It could also be easily modified to scan in consecutive circles or a circular spiral.

The invention easily equally applicable to spectral OCT in which case each scanning line produces a complete B-scan, since spectral OCT enables complete depth information to be obtained from a single scan in the X-Y plane without the need to progressively displace the coherence gate in the Z direction as is the case for time domain OCT.

It will be apparent that embodiments of the invention provide a method of scanning a patient's retina to build a volume of retinal tissue using OCT technology where it is more difficult for the patient to track the motion of the laser because the pattern of laser movement across the patient's retina discourages movement of his or her eye by ensuring the last frames scanned are those that are through the fovea.

We claim:

1. A method of building up a three dimensional OCT image of an object having a limited region sensitive to movement of a scanning beam, comprising:
    performing an OCT scan of the object, wherein said OCT scan is performed in a scanning pattern that results in said limited region being scanned last.

2. A method as claimed in claim 1, wherein said scanning pattern comprises a series of parallel scanning lines that approach said limited region from opposite sides.

3. A method as claimed in claim 2, wherein said scanning lines alternate on either side of said limited region.

4. A method as claimed in claim 3, wherein said scanning lines create horizontal B-scans.

5. A method as claimed in claim 3, wherein said scanning lines create vertical B-scans.

6. A method as claimed in claim 1, wherein said scanning pattern is in the form of a continuous contour approaching said limited region.

7. A method as claimed in claim 6, wherein said continuous contour is a spiral.

8. A method as claimed in claim 1, wherein said object is an eye, and said limited region is the fovea.

9. An apparatus for building up a three dimensional OCT image of an object having a limited region sensitive to movement of a scanning beam, comprising:
   an OCT interferometer for producing a sample beam;
   a scanner for scanning said object over the sample beam; and
   a controller for controlling said scanner to perform the scan in a scanning pattern that results in said limited region being scanned last.

10. An apparatus as claimed in claim 9, wherein said scanning pattern comprises a series of parallel scanning lines that approach said limited region from opposite sides.

11. An apparatus as claimed in claim 10, wherein said scanning lines alternate on either side of said limited region.

12. An apparatus as claimed in claim 10, wherein said scanning lines create horizontal B-scans.

13. An apparatus as claimed in claim 12, said scanning lines create vertical B-scans.

14. An apparatus as claimed in claim 9, wherein said scanning pattern is in the form of a continuous contour approaching said limited region.

15. An apparatus as claimed in claim 14, wherein said continuous contour is a spiral.

16. An apparatus as claimed in claim 15, wherein said scanner is a galvoscanner.

* * * * *